US007248704B2

(12) United States Patent
Carme et al.

(10) Patent No.: US 7,248,704 B2
(45) Date of Patent: Jul. 24, 2007

(54) ACTIVE SOUND ATTENUATION DEVICE TO BE ARRANGED INSIDE A DUCT, PARTICULARLY FOR THE SOUND INSULATION OF A VENTILATING AND/OR AIR CONDITIONING SYSTEM

(75) Inventors: Christian Carme, Marseilles (FR); Virginie Delemotte, Marseilles (FR); Pierre Chaffois, Caluire (FR); Patrick Damizet, Venissieux (FR)

(73) Assignees: Technofirst, Aubagne (FR); Aldes Aeraulique, Venissieux (FR)

( * ) Notice: Subject to any disclaimer, the term of this patent is extended or adjusted under 35 U.S.C. 154(b) by 444 days.

(21) Appl. No.: 10/286,901

(22) Filed: Nov. 4, 2002

(65) Prior Publication Data

US 2003/0053635 A1 Mar. 20, 2003

Related U.S. Application Data

(63) Continuation of application No. 09/066,353, filed as application No. PCT/FR96/01694 on May 22, 1998, now abandoned.

(30) Foreign Application Priority Data

Oct. 30, 1995 (FR) .................................. 95 12802

(51) Int. Cl.
*A61F 11/06* (2006.01)

(52) U.S. Cl. .................................... 381/71.5; 381/71.7

(58) Field of Classification Search ............... 381/71.5, 381/71.1, 71.6; 181/206; 415/119
See application file for complete search history.

(56) References Cited

U.S. PATENT DOCUMENTS

| | | | | |
|---|---|---|---|---|
| 4,596,033 | A | 6/1986 | Swinbanks | |
| 4,665,549 | A * | 5/1987 | Eriksson et al. | 381/71.5 |
| 4,876,722 | A | 10/1989 | Dekker et al. | |
| 5,498,127 | A * | 3/1996 | Kraft et al. | 415/119 |
| 5,689,572 | A | 11/1997 | Ohki et al. | |
| 5,815,582 | A * | 9/1998 | Claybaugh et al. | 381/71.6 |
| 5,828,759 | A | 10/1998 | Everingham | |
| 5,852,667 | A * | 12/1998 | Pan et al. | 381/71.5 |

FOREIGN PATENT DOCUMENTS

| | | |
|---|---|---|
| FR | 2 495 809 | 6/1982 |
| FR | 2 550 903 | 2/1985 |

* cited by examiner

*Primary Examiner*—Ping Lee
(74) *Attorney, Agent, or Firm*—Oliff & Berridge, PLC

(57) ABSTRACT

The device for the active sound attenuation of a sound signal propagated in a duct comprises: at least first sensor means for a first sound signal, attenuation actuating means supplying an active sound attenuation signal in response to a selected control signal, an electronic control means generating the active sound attenuation signal for the actuating means. The first sensor means and the actuating means are arranged completely inside the duct opposite one another and at a selected distance from the casing of the duct, the axis of symmetry of the radiation of the actuating means and the axis of symmetry of the first sensor means are substantially parallel to the direction of propagation of the sound signal in the duct, and the actuating means are arranged upstream of the first sensor means in the direction of propagation of the sound signal in the duct.

18 Claims, 7 Drawing Sheets

SECTION A-A

SECTION A-A

ACTIVE SOUND ATTENUATION DEVICE TO BE ARRANGED INSIDE A DUCT, PARTICULARLY FOR THE SOUND INSULATION OF A VENTILATING AND/OR AIR CONDITIONING SYSTEM

The present invention relates to the active sound attenuation of a sound signal propagated in a confined space, such as a duct. Active sound attenuation is the operation which involves attenuating a sound signal by electronically generating another sound signal having the same amplitude as the sound signal to be attenuated and being in phase opposition relative to the latter.

It is used, in general, in active sound attenuation installations making it possible to reduce the noise level in a selected zone, such as a duct. It is used, in particular, especially in the sound insulation of a ventilating and/or air conditioning system.

By a sound signal to be attenuated is meant, here, a noise coming from any noise source and capable of being propagated in the duct.

Patent FR-8313502 already discloses a device for the active sound attenuation of an acoustic signal propagated in a duct. In general terms, this device comprises the following means:

- a first microphone, called an error microphone, which is arranged inside the duct and which picks up a first so-called error sound signal,
- a second microphone, called a reference microphone, which is likewise arranged inside the duct, upstream of the first microphone in the direction of propagation of the sound signal in the duct, and which picks up a second so-called reference sound signal capable of being propagated in the duct,
- an attenuation source which is arranged in the wall of the casing of the duct at a selected distance from the first microphone and which supplies an active sound attenuation signal in response to a selected control signal, and
- an electronic control means suitable for generating the active sound attenuation signal for the source as a function of the first and second sound signals thus picked up.

In general terms, the electronic control means comprise filtering means, the coefficients of which are adapted, in real time, according to a selected algorithm, so as to minimize the energy of the error sound signal as a function of the reference sound signal.

The advantage of this installation is that it results in only a low pressure loss attributable solely to the presence of the error and reference microphones inside the duct.

By contrast, installing the attenuation source in the wall of the casing of the duct most often results in interference phenomena which may disrupt active attenuation. These phenomena, called "rejection phenomena", occur most often at relatively low frequencies, typically from the moment of the first angular mode of the sound waves.

In order to avoid these rejection problems, a known solution involves selecting for the electronic control means (in particular, the conditioning or antioverlap and ripple filters) a cutoff frequency below the frequency at which the sound waves of the first angular mode appear.

However, such a solution is not satisfactory and is not adopted in the present invention due to the principle of active attenuation. In fact, this principle, based on the fact that the propagation velocity of sound waves in air is higher than the propagation velocity of electricity, makes it necessary to maintain a low electric time delay at the electronic control means, this being impossible with a cutoff frequency having a low value.

A known solution conducive to an acoustic time delay (in the propagation of sound waves) greater than the electric time delay (in the propagation of electronic signals) involves arranging the reference microphone at a relatively long distance from the attenuation source. In practice, this distance is selected equal to at least four times the diameter of a circular duct.

Likewise, it is known that, in order to avoid the error microphone picking up evanescent modes coming from the attenuation source or so that these modes are sufficiently damped, it is expedient to move said attenuation source some distance from the error microphone.

The result of this is that the overall dimensions of such an installation (for example, the distance between the error microphone and the reference microphone) are selected large, thus making it bulky when it is put in place.

The same is true in the document U.S. Pat. No. 4,665,549, in which a hybrid active silencer is accommodated inside a pipeline. This document does not teach how to limit the pressure losses in the pipeline, especially how to arrange the error microphone in relation to the antinoise source so as to avoid generating interfering sound waves. Nor does this document teach how to reduce the distances between the actuating means and the sensor means (error and/or reference).

The document U.S. Pat. No. 4,876,722 also discloses another relative arrangement of the error microphone and attenuation source. This document proposes arranging the attenuation source at the center of the cross section of a duct of rectangular cross section, whilst the error microphone is arranged in the wall of the casing of the duct.

This type of installation does not provide for using the reference microphone in order to participate in the preparation of the attenuation sound signal. It involves simple filtering by negative feedback. Moreover, here, the axis of symmetry of the radiation of the attenuation source is perpendicular to the direction of propagation of the sound waves, thus limiting the efficiency of active sound attenuation, since this asymmetric arrangement generates interference sound waves (equivalent to those of the first angular mode or "transverse mode") from the moment of the frequency at which such a mode appears. Where appropriate, this arrangement is effective for processing the transverse mode only.

The document FR-81-22406 discloses an active sound attenuation installation, in which the attenuation source supplies its attenuation signal in the duct by way of a waveguide.

Such an installation has the disadvantage of being heavy and bulky to put in place, especially on account of the coupling means between the duct to be insulated against sound and the waveguide.

Finally, the document FR-A-2275722 describes a device comprising a reference microphone and an antinoise source which are arranged inside a pipeline. There is no error microphone placed in the vicinity of the antinoise source. The device, therefore, is not adaptive. It does not make it possible to obtain satisfactory attenuations when the physical parameters of the pipeline (temperature, soiling, etc.) change.

The present invention aims to improve prior active sound attenuation installations.

Its object is especially to provide an active sound attenuation device, which is easy and not very bulky to put in place inside the duct and which results in a low pressure loss in the duct, whilst at the same time avoiding the generation of interference sound waves.

It relates to a device for the active sound attenuation of a sound signal propagated in a duct, the device comprising, at least first sensor means arranged at a first location inside the duct and suitable for picking up a first sound signal at least at one point of said first location, attenuation actuating means which are arranged in a predetermined geometric relation relative to the duct and upstream of the first sensor means in the direction of propagation of the sound signal in the duct and which are suitable for supplying an active sound attenuation signal in response to a selected control signal, and electronic control means suitable for generating the active sound attenuation signal for the actuating means, in order to minimize the energy of the first sound signal thus picked up.

According to a general definition of the invention, the first sensor means and the actuating means are separated from one another by a short distance substantially smaller than the diameter or than the smallest dimension of the cross section of the duct and are arranged completely inside the duct at a selected distance from the casing of the duct, and the axis of symmetry of the radiation of the actuating means and the axis of symmetry of the first sensor means are substantially parallel to the direction of propagation of the sound signal in the duct.

Such an arrangement makes it possible to process the plane wave so as to avoid the appearance of interfering sound waves, especially those of the first angular mode, without thereby resorting to too low a cutoff frequency which would bring about too great an electric time delay. The result of this is that it is no longer necessary, according to the invention, to move the actuating means a distance of high value from the first sensor means (error microphone). Thus, the device according to the invention is easy and not very bulky to put in place, as are, where appropriate, second sensor means (reference microphone) which will be described in more detail later.

Highly advantageously, the first sensor means and the actuating means are arranged substantially in the central axis of the duct.

According to another aspect of the invention, the device comprises a fixed framework (or bulb) which is capable of supporting the actuating means and the first sensor means according to a selected arrangement making it possible to avoid generating interfering sound waves and the dimensions and shape of which are selected in order to limit the pressure loss in the duct.

Preferably, the framework supports passive sound attenuation means which are arranged according to a selected arrangement for facilitating the directivity of the radiation of the actuating means and the volume of which is optimized by virtue of active attenuation so as to limit the pressure loss and reduce the bulk of the device in the duct.

According to another aspect of the invention, fastening means for fastening the framework inside the duct are provided at a selected distance from the casing of said duct, the dimensions and shape of said means being selected so as to limit the pressure loss in the duct.

Highly advantageously, the framework is in one piece, has a low pressure loss and is compact.

According to another embodiment of the invention, there are provided, furthermore, second sensor means which are arranged at a second location inside the duct, upstream of the first location in the direction of propagation of the sound signal in the duct, and in which are suitable for picking up a second sound signal at least at one point of said second location, the electronic control means generating the active sound attenuation signal for the actuating means, in order to minimize the energy of the first sound-signal, as a function of the first and second sound signals thus picked up.

Such a device constitutes an active sound attenuator of the type with advance filtering (also called FEED FORWARD CONTROL).

In practice, the framework supports the second sensor means inside the duct at a selected distance from the casing of the duct and from the actuating means.

Preferably, at the location of contact with the casing of the duct, the fastening means are covered with a vibration damping material.

According to another aspect of the invention, the electronic control means comprise filtering means, the coefficients of which are adapted, in real time, according to a selected algorithm, in order to minimize the energy of the first sound signal as a function of the second sound signal.

Alternatively, the duct is subdivided into a plurality of subducts with or without a casing (with or without partitioning), each subduct having associated with it a framework which is arranged inside said subduct, the plurality of frameworks forming a single structure with or without passive attenuation means. Such a device constitutes a multichannel system.

In practice, the plurality of frameworks is arranged substantially in the central axis of the duct. For example, at least one of the frameworks of said plurality is arranged substantially in the central axis of the duct.

If the multichannel system is coupled, electronic control means are common to the plurality of frameworks.

If the multichannel system is uncoupled, the electronic control means are subdivided into independent electronic control submeans, each associated with the actuating means and the sensors of each framework.

If appropriate, for the coupled or uncoupled systems, the second sensor means are common to the plurality of frameworks.

According to another characteristic of the device according to the invention, the duct casing located at a selected distance from the source and at least from the first sensor means comprises passive sound attenuation means for the casing.

Other characteristics and advantages of the invention will emerge from the following detailed description and from the drawings in which.

Figures 1, 2:
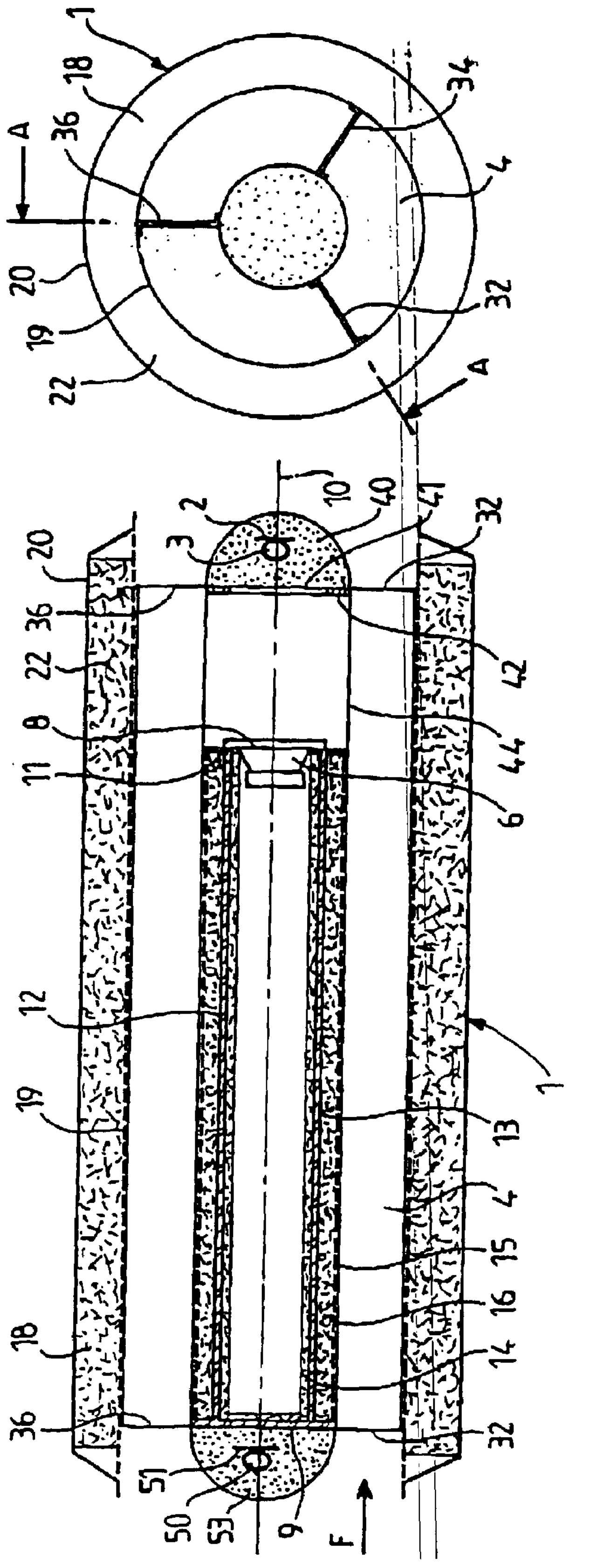
FIG. 1 is a sectional view along the axis A-A of the essential means constituting the device according to the invention.
FIG. 2 is a front view of the device according to the invention arranged inside a circular duct.

Referring to FIG. 1, the active sound attenuation device according to the invention is used in a nonlimiting way and preferably for the sound insulation of a ventilation casing, the technical characteristics of which are, for example, as follows:

- circular duct, the total diameter of which varies from 125 mm to 1250 mm;
- fluid flowing inside the duct: air, the temperature of which may vary from +10° to +50° with a relative humidity of 40 to 100%;
- during injection, the air may be filtered, whilst, during extraction, the air is not filtered and may contain fatty vapors, particularly when the circular duct is of the VMC type in a dwelling.

This is, of course, a nonlimiting example of use. The device according to the invention is also used for ducts of oblong, square, rectangular or such like cross section. The fluid may be not only air, but also another gas or water. There may or may not be fluid flow.

The device according to the invention may be installed at any orifice between a noisy location and a location to be insulated against sound.

For example, the device according to the invention is used for a ventilation unit, for example the unit VEC271B sold by the company ALDES.

The electronic control means which supply the active sound attenuation signal to the antinoise source preferably employ the technique of advance filtering, also called FEED FORWARD CONTROL. However, the essential characteristics of the device, namely especially its particular arrangement inside the duct, may also apply to retroacting filtering means, also called FEED BACK CONTROL.

The rest of the description will concentrate on describing the filtering means of the advance type. However, the description relating to the device according to the invention may also apply equally to a device in which the electronic control means are of the type with retroacting filtering.

It is recalled that, in retroactive filtering means, only an error sensor and an antinoise source are provided, whilst, in the case of electronic control means employing advance filtering means, there is provided, furthermore, a reference sensor which is mounted upstream and which supplies a reference sound signal.

The essential means constituting the device according to the invention will now be described in detail.

Referring to FIGS. 1 and 2, the device comprises a sensor 2 arranged at a location 3 inside the core 4 of a circular duct 1. This sensor picks up a first sound signal e (called an error signal) at least at one point 3 of the duct.

An attenuation source 6 is arranged inside the core 4 of the duct. This source supplies an active sound attenuation signal in response to a selected control signal which will be described in more detail later.

Electronic control means (not shown in FIGS. 1 and 2) generate the active sound attenuation signal for the source as a function of at least the first sound signal e.

It should be noted, from now on, that the first sensor means 2 and the source 6 are arranged completely inside the duct opposite one another and at a selected distance from the casing of the duct.

It should also be noted that the axis of symmetry of the radiation of the source and the axis of symmetry of the first sensor means are substantially parallel to the direction of propagation of the sound signal in the duct.

Figure 3:
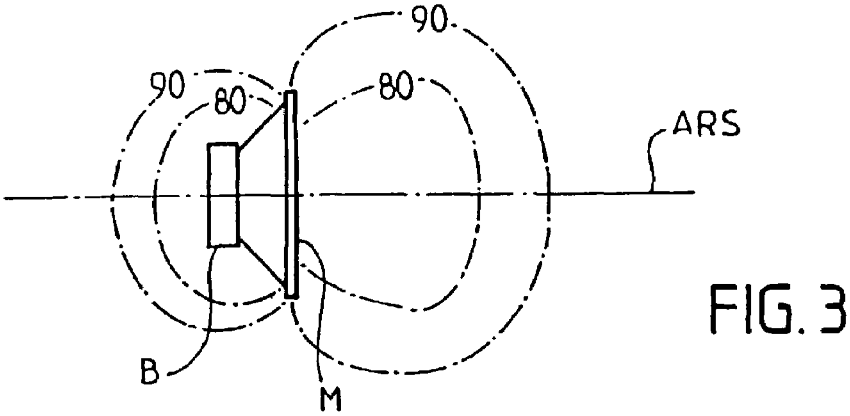
FIG. 3 shows diagrammatically the isoeffectiveness curves of a directional loudspeaker.

Referring to FIG. 3, the source is a loudspeaker with diaphragm M and coil B. The axis of radiation of the loudspeaker ARS, here, is the main axis of the loudspeaker, upon which the physical quantities (intensity, output, pressure) are maximum.

Figure 4:
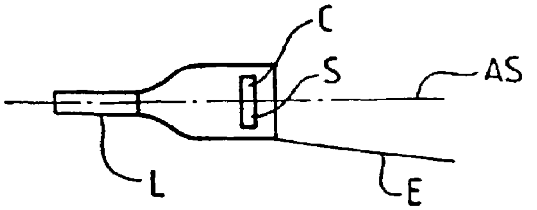
FIGS. 4 and 5 show diagrammatically the essential elements of a microphone and its isosensitivity curves.
Figure 5:
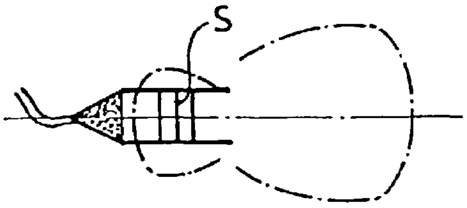

Referring to FIGS. 4 and 5, the first sensors 2 comprise at least one unidirectional microphone S formed from a sensitive capsule C, itself sheathed in a protective sheathing E. The axis of symmetry AS of the microphone is shown. The microphone is connected to the electronic control means by way of conventional cables L. The isosensitivity curves are likewise shown in FIG. 5.

Reference is made once again to FIGS. 1 and 2. It should also be noted that the source 6 is arranged upstream of the sensor 2 in the direction of propagation of the sound signal in the duct, said propagation being represented by the arrow F.

Advantageously, here, the sensor 2 and source 6 are arranged substantially in the central axis 10 of the duct.

According to the invention, arranging the source and the sensor inside the duct and according to the arrangement described above affords many advantages.

First of all, arranging the active attenuation device completely (with the exception, where appropriate, of the electronic control means) in the environment to be insulated against sound avoids generating an interfering rejection zone, as in the patent FR-83 13502 mentioned above.

In fact, contrary to an arrangement of the source in the casing, the sound vibrations caused by the source according to the invention are taken into account completely by the electronic control means.

Next, as will also be seen in more detail later, the sensor means (microphone) and actuating means (loudspeaker) of the device according to the invention are supported inside the duct by a framework (or bulb), the shape and dimensions of which are selected especially for the purpose of avoiding the appearance of interfering sound waves and of limiting the pressure loss of the duct.

Moreover, this framework is fastened inside the duct by fastening means which are covered, as regards the parts in contact with the casing of the duct, with a material having vibration damping properties. Contrary to an arrangement of the source fastened to the casing, these vibration damping means are easy to put in place.

According to another aspect of the invention, the source 6 is accommodated at the end 11 of a sound column 12. For example, the column is of cylindrical shape. The source 6 is arranged at one 11 of the ends of the cylinder, in such a way that the radiating surface of the source is opposite the error microphone 2.

The column consists of a rigid material, for example of PVC, or of sheet metal.

For example, the length of the sound column is of the order of 800 to 1000 mm. Its diameter is of the order of 100 to 300 mm. The distance between the radiating surface of the loudspeaker 6 and of the microphone 2 is of the order of 150 to 300 mm.

Other dimensions, would, of course, be suitable, depending on the selected uses and the dimensions of the ducts.

The inner wall 14 of the sound column 12 is advantageously covered with a passive absorption material. For example, this passive sound absorption material is rockwool. For example, the thickness of the rockwool, here, is of the order of 10 to 30 mm.

The sound column 12 is itself supported by a framework 16 of cylindrical shape, such as a shell or bulb. The outer wall 15 of the framework 16 consists of a perforated rigid material conducive to passive absorption and avoiding the erosion of the rockwool by the airstream. In practice, the rigid material of the shell is a perforated metal sheet.

The rate of perforation is at least of the order of 30% per unit area. Perforation is conducive to the absorption of sound energy since the rockwool comes into contact with the environment in which the sound waves are propagated.

Highly advantageously, the space between the outer wall 15 of the framework and the outer wall 13 of the column 12 is filled with rockwool.

Highly advantageously, the interior wall 19 of the casing 18 of the duct is likewise provided with passive sound attenuation means. For example, the interior wall 19 of the casing 18 consists of a material, such as perforated sheet metal. A passive sound attenuation material is advantageously accommodated between the interior wall 19 and the exterior wall 20 of the casing 18 of the duct. In practice, this passive sound attenuation material is also rockwool. The thickness of the rockwool is of the order of 25 to 50 mm, and its density is of the order of 40 $kg/m^3$ to 70 $kg/m^3$.

It should be noted that that part of the casing of the duct which is equipped with passive sound attenuation means opposite the bulb improves the overall attenuation of the device according to the invention within a wide frequency band. This part of the casing is most often intended to be assembled together with another casing having no passive attenuation.

Highly advantageously, the sensor 2 is a microphone embedded in a hemisphere 40 consisting of a material which advantageously has transparent sound properties. This material is, for example, open-cell foam. This material makes it possible to avoid interfering ventilation turbulences, this being conducive to a good pickup of the sound signal.

The hemisphere 40 is supported by a ring 42 arranged at a selected distance from the source 6 by means of two feet 44, the length of which determines the distance separating the radiating surface of the source and the equatorial face 41 of the hemisphere 40.

The space between the radiating surface of the source and the face 41 may be empty or else filled or partially delimited with open-cell foam or other acoustically transparent material.

It is expedient to note, however, that the space in contact with the diaphragm of the loudspeaker must be free, so as to avoid interfering vibrations.

Alternatively, the space between the source 6 and the sensor 2 is delimited by a fabric of small thickness or a thin layer of open-cell foam. These materials are advantageously acoustically transparent. Here, the "acoustically transparent" property affords the advantage of improving the filtering of turbulences for the error microphone 2. It likewise improves the filtering of dust. It also avoids breakaways of the ventilation stream.

As seen above, the electronic control means are advantageously, but in a nonlimiting way, of the type with advance filtering means.

In this case, a reference sensor 50 is provided, which is arranged at a second location 51 of the duct, upstream of the first location 3 in the direction of propagation of the sound signal in the duct. This sensor 50 is suitable for picking up a second sound signal at least at a point 51 of the duct. This second sound signal constitutes the reference signal r which the electronic control means will employ.

Highly advantageously, this sensor 50 is arranged in the vicinity of that end 9 of the column 12 which is longitudinally opposite that end 11 of the sound column 12 into which the source is inserted.

The sensor 50 is likewise embedded in a hemisphere 53 made from open-cell foam. The hemisphere 53 is laid against the end 9 of the sound column 12.

The framework 16 and the sensors 2 and 50 are held inside the duct by fastening means which are composed of fins 32, 34 and 36 extending along the framework from level with the equatorial face 41 of the hemisphere 40 to level with the end 9 of the column 12. These fastening means make it possible to fasten the framework at a selected distance from the casing of the duct.

It should be noted that these fins may be individual or form a kind of spider with three branches, thus making it possible to form a common fastening for the source and the sensors. This common fastening makes it possible for the sound attenuation device according to the invention to be put in place easily. Moreover, it is not very bulky and has an aerodynamic shape which does not increase the pressure loss in the duct.

Highly advantageously, the ends of the fins at the location of contact with the casing of the duct are covered with a vibration damping material, for example a material of the elastomeric type.

Arranging the active sound attenuation device according to the invention inside the duct inevitably results in a pressure loss. It is expedient if this pressure loss is relatively negligible, for example below 20 Pa for an average velocity of the air in the duct of 5 m/s.

In order to adhere to such a pressure loss for circular cross sections, the ratio between the outside diameter of the framework and the inside diameter of the duct must remain substantially below 0.6. For noncircular cross sections, it is expedient to make sure of adhering to a ratio between the cross section of the framework and the cross section of the core of the duct which is substantially lower than 0.33.

It is expedient to recall that, due to the arrangement of the device according to the invention inside the duct and the particular arrangement of the sensor and actuating means, the dimensions of the framework are of the order of 1 m to 1.3 m. In fact, arranging the framework inside the duct make it possible to avoid the appearance of sound waves of the first and second angular propagation modes, that is to say frequencies of the order of a few hundred Hertz.

This is a very important advantage, since it makes it possible, under these conditions, to reduce the dimensions of the framework, this also being conducive to a low bulk of the sound attenuation device according to the invention.

Likewise, installing the framework at the center of the duct makes it possible to shorten the distance separating the error microphone 2 and the attenuation loudspeaker 6. However, in light of an evanescent propagation of some sound waves, it is expedient to maintain the loudspeaker at a distance from the error microphone of the order of 15 to 30 cm.

Moreover, due to the particular arrangement of the sensor means and actuators according to the invention, the minimum theoretical distance between the loudspeaker 6 and the reference microphone 50 corresponds to two diameters of the duct. This minimum theoretical distance must be compared with a theoretical length equivalent to four diameters in the case of a source arranged in the wall of the casing of the duct, as in the patent FR-83 13502 mentioned above.

It should be noted that the abovementioned advantages are valid as regards positioning the diaphragm of the loudspeaker at the center of gravity of the latter. Under these conditions, the radiating surface of the loudspeaker may be perpendicular to the direction of propagation of the sound waves, but also parallel or at a particular angle. However, the loudspeaker is actually directional when the radiating surface of the loudspeaker is substantially perpendicular to the direction of propagation of the sound waves.

On the other hand, the complementarity of the passive attenuation elements improves directivity all the more since the sound waves are propagated upstream from the attenuation source, for example are damped by the passive device. Moreover, the active sound attenuation device according to the invention is symmetric relative to the axis of symmetry of the duct when the radiating surface of the attenuation source is substantially perpendicular to the direction of propagation of the sound waves.

Now since the angular modes are asymmetric, they risk being excited slightly by a loudspeaker being placed asymmetrically.

For example, the loudspeaker is that sold by the company AUDAX under the reference HT 130k0.

The control and reference microphones are, for example, unidirectional microphones sold under the reference EM357 by the company POOKOO INDUSTRIAL.

Figure 7:
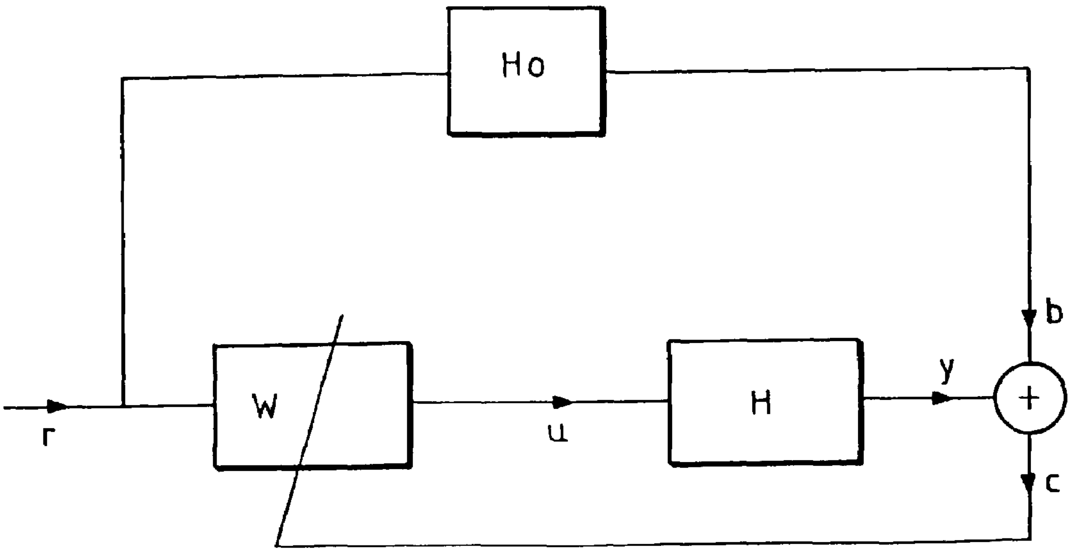
FIG. 7 is an equivalent diagram of the electronic control means according to the invention.
Figure 6:
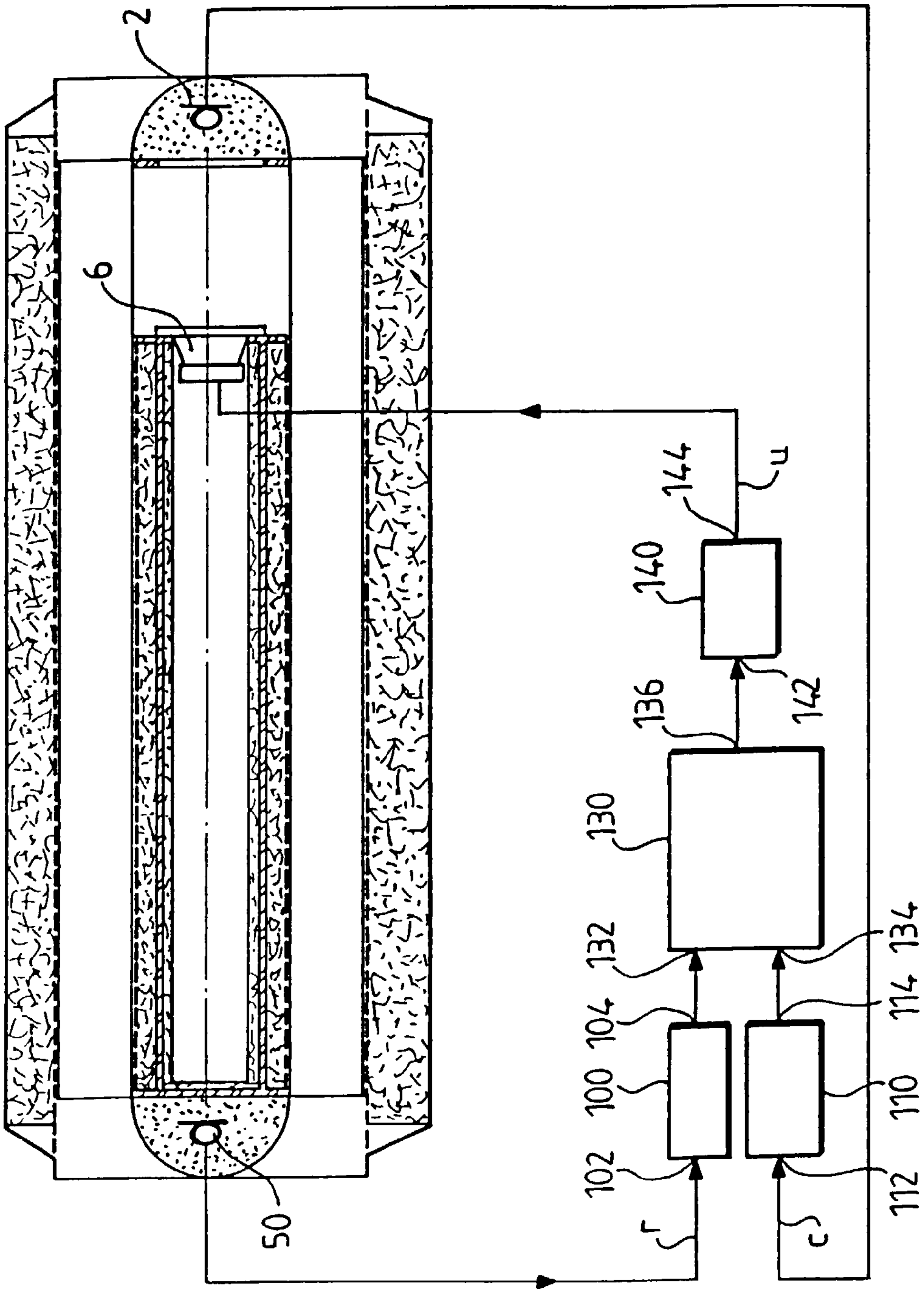
FIG. 6 illustrates diagrammatically the electronic control means of the device according to the invention.

Reference is now made to FIGS. 6 and 7 which illustrate diagrammatically the architecture and functional aspect of the electronic active attenuation control means according to the invention with regard to a single-channel system.

In general terms, here, the electronic control means which will be capable of generating the active sound attenuation signal of the source 6 are articulated about advance filtering means. These control means are advantageously accommodated inside the framework. They may also be accommodated in the casing of the duct.

These advance filtering means comprise a first acquisition block 100 possessing an input 102 connected to the sensor 50 and an output 104. Likewise, there are provided for the sensors 2 an acquisition block 110, possessing an input 112 connected to the sensor means 2, and an output 114.

These acquisition blocks 100 and 110 convey their respective signals to a processor 130 possessing an input 132 connected to the input 104 and an input 134 connected to the output 114.

The processor 130 is advantageously a processor of the type DSP for DIGITAL SIGNAL PROCESSOR. For example, the processor 130 is that sold by the company TEXAS INSTRUMENTS under the reference TMS 320C25.

The processor 130 possesses an output 136 supplying a digital signal to a restitution block 140. This block 140 possesses an input 142 connected to the output 136 and an output 144 connected to the source 6.

The acquisition blocks 100 and 110 are blocks for the acquisition of an analog signal in order to convert it into a digital signal for the processor 130.

In general terms, each acquisition block 100 and 110 comprises a preamplification element followed, in series, by a conditioning filter, for example an anti-overlap filter, and, finally, by an analog/digital converter.

Conversely, the restitution block 140 is a device, the function of which is to ensure the conversion of a digital signal into an analog signal.

In general terms, such a restitution block comprises a digital/analog converter followed by a ripple filter, for example a low-pass filter, and by an audio amplifier.

The processor 130 is capable of monitoring a minimizing algorithm, in such a way that the signal e picked up by the sensor 2 has the lowest possible energy. This action is carried out by supplying a signal u which excites the attenuation source 6 in such a way that the antinoise wave emitted by the source 6 has the same amplitude as the signal picked up by the sensor 50, but in phase opposition relative to the latter, so as to attenuate the noise which is propagated in the duct from the location 51 to the location 3.

In practice, the minimizing algorithm is an algorithm of the type LMS for LEAST MEAN SQUARE.

The sampling frequency of the analog/digital converters is carefully selected so as to avoid introducing a time delay detrimental to the level of propagation of the electronic signals.

In the operating state, that is to say during the minimizing phase, the processor periodically acquires, in real time, the reference noise r picked up by the sensor 50. These processing means likewise calculate the energy of the signal e picked up by the error sensor 2. Subsequently, the advance filtering means are set in search of the optimum parameters W for the best active attenuation, in order, in real time, to determine the values of the active sound attenuation control signal u.

Before that, however, it is expedient to know exactly the pulse responses of the device according to the invention.

Referring to FIG. 7, the pulse responses involved are the pulse response Ho relating to the transfer function between the sensor 50 and the source 6 and the pulse response H relating to the transfer function between the source 6 and the error sensor 2.

The transfer function H comprises an input for receiving the signal u and an output supplying the signal y which corresponds to the active sound attenuation signal picked up by the sensor 2.

The transfer function Ho comprises an input for receiving the signal r and an output supplying the signal b which corresponds to the sound radiation of the source to be attenuated and which is picked up by the reference sensor 50. The function Ho is most often advantageously negligible.

The transfer function H is measured as follows.

In a first initialization step, the transfer function of the so-called secondary path between the source 6 and the error microphone 2 is measured by means of an initialization method, for example by exciting the source 6 by filtered DIRAC type white noise reference signals or the like.

The transfer function H is sampled and safeguarded in the memory DSP processor. For example, the transfer function is sampled at the frequency of 5400 Hz over a number of 70 points.

It is likewise used for the abovementioned transfer function Ho.

The digital filtering coefficients W are adapted, in real time, according to the LMS algorithm in order to minimize the signal e as a function of the signal r (or b).

Thus, the device according to the invention functions independently of the setting of the installation, of the flowrate and of the velocity of the fluid in the duct or of the ventilation system accessories present upstream or downstream of the device according to the invention.

Likewise, here, the iterative minimizing algorithm of the LMS type makes it possible to find active attenuation, whatever the type of noise source, for example fans or compressors or the like. Likewise, since the pulse responses are previously measured, the implementation and adaptation of the installation are very simple and do not involve acoustics or electronics specialists.

It is expedient to note that the device according to the invention is designed with passive attenuation incorporated in it where appropriate, thus making it possible to obtain very useful performances over the entire audible frequency band.

In some configurations, called multichannel systems, it may be necessary to insert a plurality of frameworks in the duct. In that case, a distinction is made between two categories of multichannel systems: the coupled system and the uncoupled system.

Figure 8:
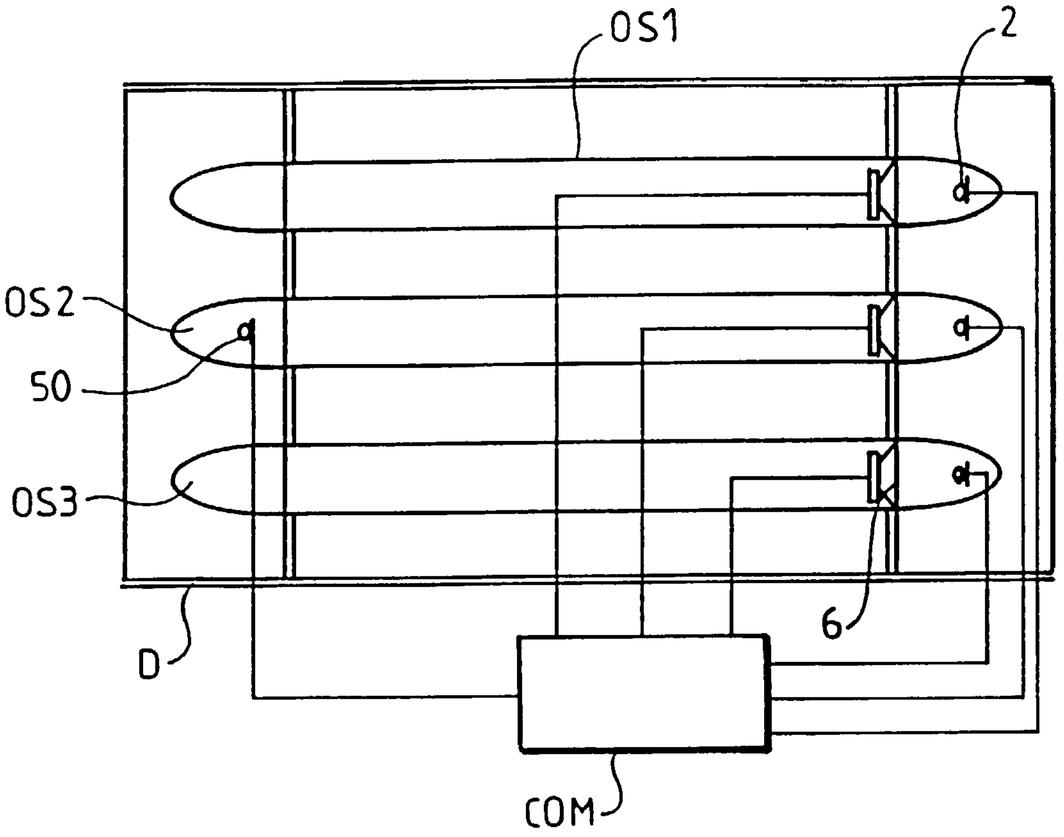
FIGS. 8 and 9 illustrate diagrammatically a coupled multichannel system according to the invention.
Figure 9:
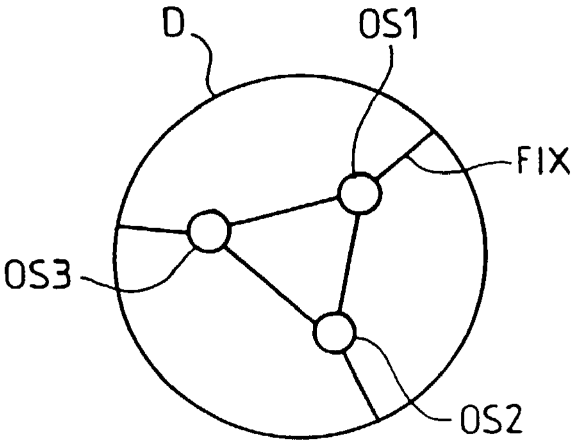

In the coupled system (FIGS. 8 and 9), there is provided a number z of frameworks OS, here individualized at OS1 to OS3, such as those described above, each with at least one error microphone 2 and at least one loudspeaker 6. There are therefore n error microphones (here n=3) and m number of loudspeakers (here m=3). The frameworks each treat a space inside the duct D. The fastening means FIX for each framework are interwoven in the duct in the manner of a spider's web. These fastening means FIX are the fins 32 described with reference to FIGS. 1 and 2.

Each framework may have associated with it a respective reference microphone 50 or a single reference microphone for the plurality of frameworks.

Electronic control means COM are common to the plurality of frameworks. They acquire the n×m pulse responses Hij (i being an integer varying from 1 to n and j being an integer varying from 1 to m) over a selected number of points and at a selected sampling frequency.

The electronic control means also acquire the n pulse responses Hoi in order to take into consideration the sound propagation between the error microphones and the reference microphones. Finally, in real time, they calculate the n filters Wi. Each of the filters and consequently each control signal are dependent on the signals picked up by the reference microphone or microphones and the error microphones and on the pulse responses.

Figure 10:
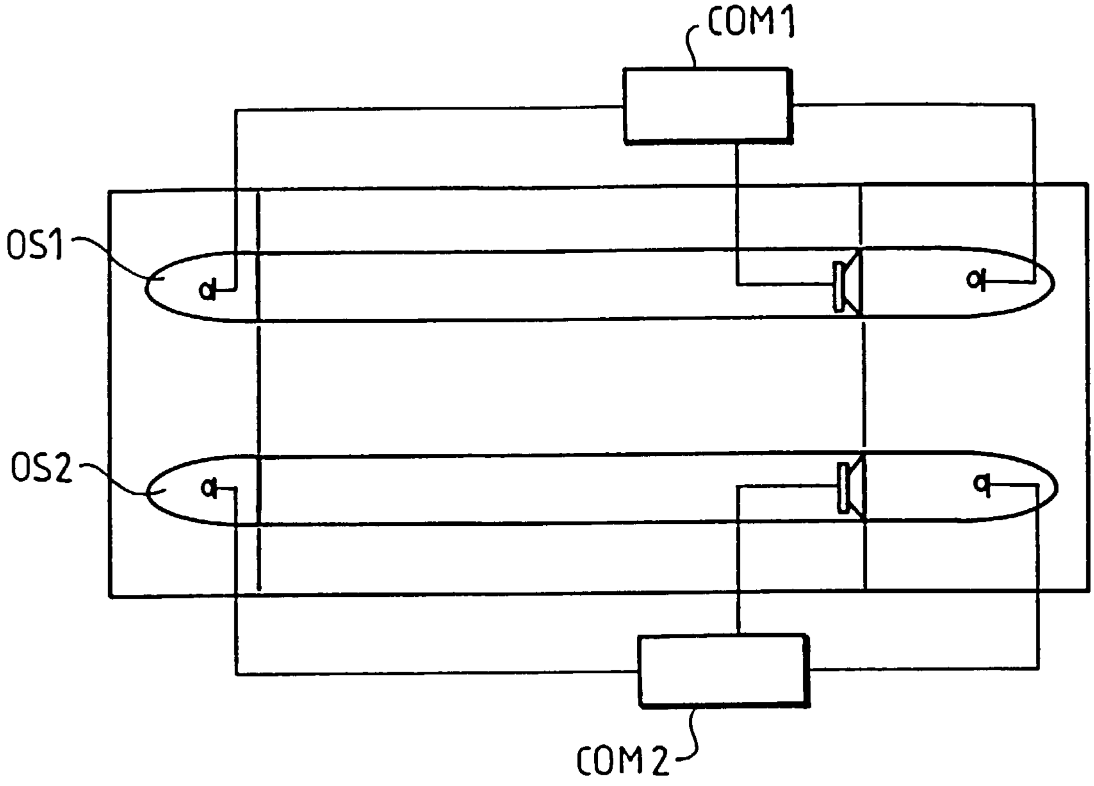
FIGS. 10 and 11 illustrate diagrammatically an uncoupled multichannel system without partitioning according to the invention.
Figure 11:
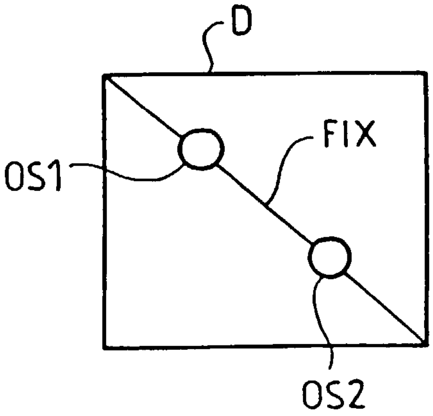
Figure 12:
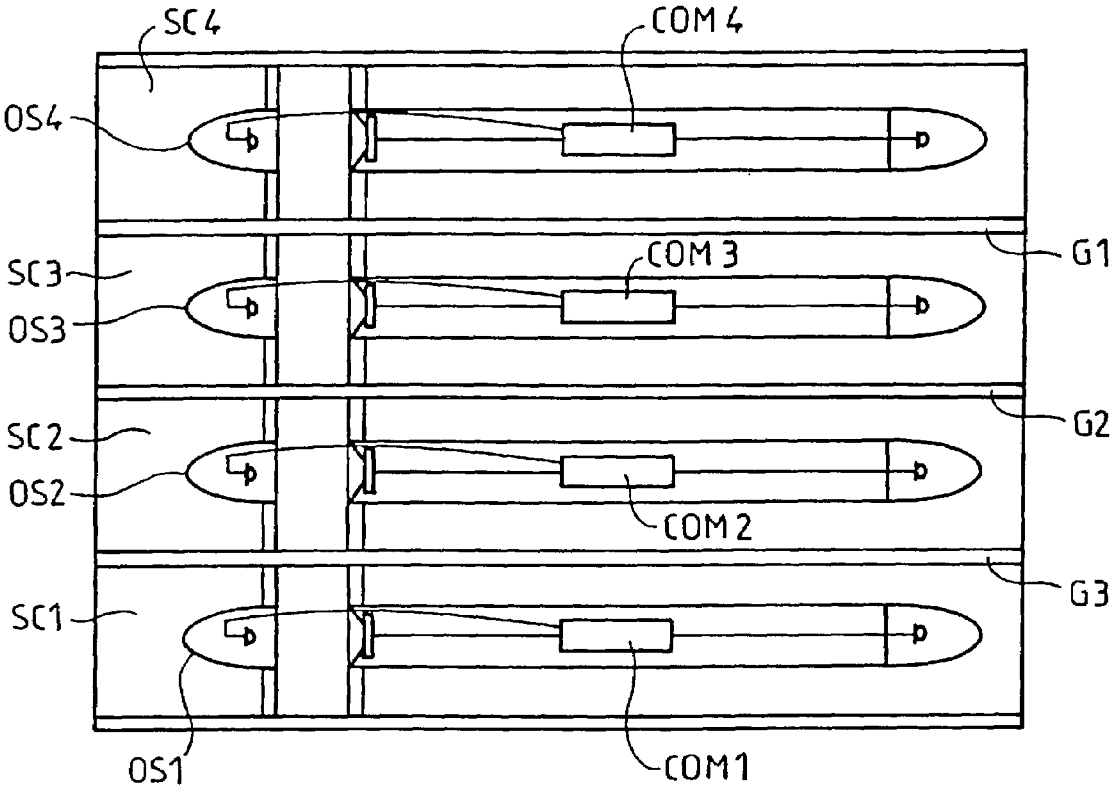
FIGS. 12 and 13 illustrate diagrammatically an uncoupled multichannel system with partitioning according to the invention.
Figure 13:
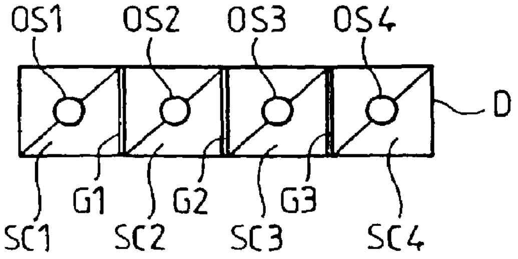

In the uncoupled system (FIGS. 10, 11, 12 and 13), the n error microphones and the m loudspeakers are positioned in n subducts with a casing (FIGS. 12 and 13) or without a casing (FIGS. 10 and 11). The n subducts, when grouped together, correspond to the total duct D. Here, the casings G1 to G3 of the subducts SC1 to SC4 are separate from the framework fastening means. If appropriate, the fastening means, if they are solid over the entire length of the device, may constitute the casings of the subducts.

In the uncoupled state, the electronic control means are subdivided into electronic control submeans COM1 and COM2 which are each associated with the actuating means and sensors of each framework OS1 and OS2.

Provision may be made for the second sensor means to be common to the plurality of frameworks.

The means for fastening each framework thus constitute a partitioning of the duct, said partitioning being capable of being modified, as desired, depending on the selected use.

Figure 14:
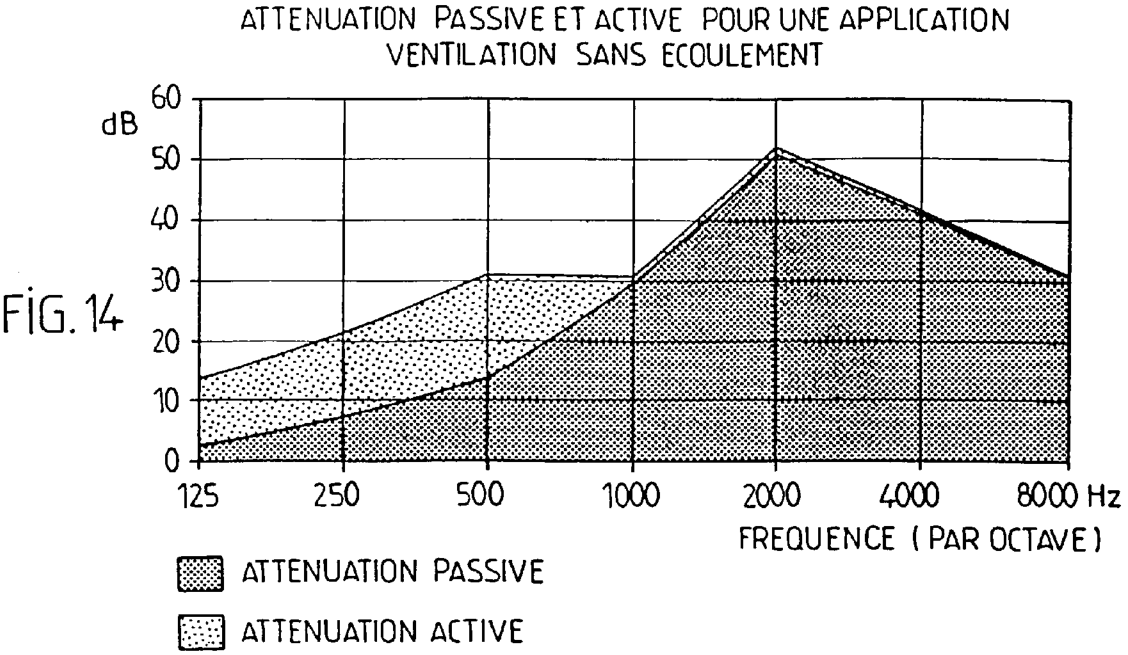
FIGS. 14 and 15 are curves illustrating the results obtained by means of a single-channel device according to the invention.
Figure 15:
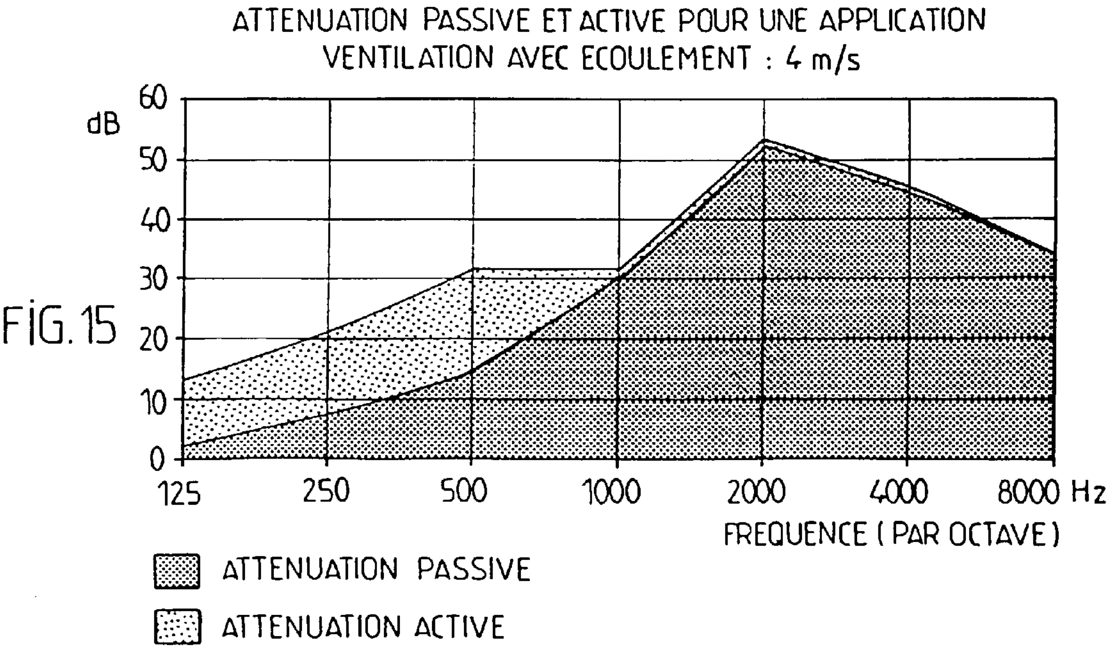

Referring to FIGS. 14 and 15, active and passive attenuation results were obtained respectively with and without flow in the duct. The attenuation curves were measured on a pipe of a diameter of 315 mm comprising passive and active absorption, as described with reference to FIGS. 1 to 7.

These measures were carried out according to the standard by insertion by means of a certifying authority.

In the case of a purely random noise, the attenuation of the device according to the invention at low frequencies is 10 dB at 125 Hz, 12 dB at 250 Hz and 15 dB at 500 Hz.

Likewise, the optimized association of wideband active sound absorption and of passive absorption makes it possible to obtain a satisfactory result for low frequencies, that is to say those below 1000 Hz in the case of random noise. The sound attenuation obtained is 13 dB at 125 Hz, 20 dB at 250 Hz and 30 dB at 500 Hz.

Moreover, it is appropriate to note that the volume occupied by the passive attenuation means is of relatively little bulk, as compared with prior structures, so as to limit the pressure loss and reduce the bulk of the device in the duct. This reduced volume is optimized, here, due to the choice of the parameters of active attenuation according to the invention.

What is claimed is:

1. A device for the active sound attenuation of a sound signal propagated in a duct, the device comprising:

at least first sensor means which are arranged at a first location inside the duct for picking up a first sound signal at least at one point of said first location, attenuation actuating means which are arranged in a predetermined geometric relation relative to the duct and upstream of the first sensor means in a direction of propagation of the sound signal in the duct for supplying at least one active sound attenuation signal in response to at least one selected control signal, electronic control means for generating the active sound attenuation signal for the actuating means, in order to minimize energy of the first sound signal thus picked up, and a fixed framework supporting the actuating means and the first sensor means according to a selected arrangement to avoid generating interfering sound waves, the fixed framework including dimensions and a shape selected so as to limit a pressure loss in the duct, wherein the first sensor means and the actuating means are separated from one another by a distance substantially smaller than the diameter or than the smallest dimension of a cross section of the duct, in order to avoid the first sensor means receiving interfering sound waves from the actuating means including a first angular mode sound wave, and arranged completely inside the duct at a selected distance from an inner wall of a casing of the duct, wherein an axis of symmetry of a radiation of the actuating means and an axis of symmetry of the first sensor means are substantially parallel to the direction of propagation of the sound signal in the duct, and wherein the first sensor means and the actuating means are arranged substantially in a central axis of the duct.

2. The device as claimed in claim 1, wherein the framework supports passive sound attenuation means arranged according to an arrangement selected to facilitate the directivity of the radiation of the actuating means, limit the pressure loss and optimize active attenuation.

3. The device as claimed in claim 1, comprising, furthermore, fastening means for fastening the framework inside the duct at a selected distance from the inner wall of the casing of said duct, the dimensions and shape of said fastening means being selected so as to limit the pressure loss in the duct.

4. The device as claimed in claim 3, wherein, at the location of contact with the inner wall of the casing of the duct, the fastening means are covered with a vibration damping material.

5. The device as claimed in claim 1, wherein the framework is in one piece, has a low pressure loss and is compact.

6. The device as claimed in claim 1, wherein the framework supports second sensor means inside the duct at a selected distance from the inner wall of the casing of the duct and from the actuating means.

7. The device as claimed in 1, wherein the duct casing located at a selected distance from the actuating means and at least the first sensor means comprises passive sound attenuation means for the casing.

8. The device as claim in 1, wherein the electronic control means comprise filtering means having coefficients, and wherein the coefficients are adapted in real time to minimize the energy of the first sound signal as a function of a second sound signal outputted by a second sensing means disposed upstream, relative to the direction of propagation of the sound stream, from the attenuation actuating means.

9. A device for the active sound attenuation of a sound signal propagated in a duct, the device comprising:

at least first sensor means which are arranged at a first location inside the duct for picking up a first sound signal at least at one point of said first location, attenuation actuating means which are arranged in a predetermined geometric relation relative to the duct and upstream of the first sensor means in a direction of propagation of the sound signal in the duct for supplying at least one active sound attenuation signal in response to at least one selected control signal, electronic control means for generating the active sound attenuation signal for the actuating means, in order to minimize energy of the first sound signal thus picked up, and second sensor means which are arranged at a second location inside the duct, upstream of the first location in the direction of propagation of the sound signal in the duct, for picking up a second sound signal at least at one point of said second location, and wherein the electronic control means generate the active sound attenuation signal for the actuating means, in order to minimize the energy of the first sound signal as a function of the first and second sound signals thus picked up, wherein the first sensor means and the actuating means are separated from one another by a distance substantially smaller than the diameter or than the smallest dimension of a cross section of the duct, in order to avoid the first sensor means receiving interfering sound waves from the actuating means including a first angular mode sound wave, and arranged completely inside the duct at a selected distance from an inner wall of a casing of the duct, and wherein an axis of symmetry of a radiation of the actuating means and an axis of symmetry of the first sensor means are substantially parallel to the direction of propagation of the sound signal in the duct.

10. The device as claimed in claim 9, wherein the second sensor means and the actuating means are separated from one another by a distance substantially greater than or equal to two diameters or the smallest dimension of the cross section of the duct and substantially smaller than four diameters or the smallest dimension of the cross section of the duct.

11. The device as claimed in claim 9, wherein the electronic control means comprise filtering means, coefficients of which are adapted, in real time, according to a selected algorithm in order to minimize the energy of the first sound signal as a function of the second sound signal, a plurality of frameworks forming a single structure with or without passive attenuation means.

12. A device for the active sound attenuation of a sound signal propagated in a duct, the device comprising:

at least first sensor means which are arranged at a first location inside the duct for picking up a first sound signal at least at one point of said first location, attenuation actuating means which are arranged in a predetermined geometric relation relative to the duct and upstream of the first sensor means in a direction of propagation of the sound signal in the duct for supplying at least one active sound attenuation signal in response to at least one selected control signal, and electronic control means for generating the active sound attenuation signal for the actuating means, in order to minimize energy of the first sound signal thus picked up, wherein the first sensor means and the actuating means are separated from one another by a distance substantially smaller than the diameter or than the smallest dimension of a cross section of the duct, in order to avoid the first sensor means receiving interfering sound waves from the actuating means including a first angular mode sound wave, and arranged completely inside the duct at a selected distance from an inner wall of a casing of the duct, wherein an axis of symmetry of a radiation of the actuating means and an axis of symmetry of the first sensor means are substantially parallel to the direction of propagation of the sound signal in the duct, and wherein the duct is subdivided into a plurality of subducts with or without a casing, each subduct having an associated framework arranged inside said subduct, the plurality of frameworks forming a single structure with or without passive attenuation means.

13. The device as claimed in claim 12, wherein the plurality of frameworks is arranged substantially in the central axis of the duct.

14. The device as claimed in claim 12, wherein at least one of the frameworks of the plurality of frameworks is arranged substantially in the central axis of the duct.

15. The device, as claimed in claim 12, wherein the electronic control means are common to the plurality of frameworks.

16. The device as claimed in claim 12, wherein the electronic control means are subdivided into independent electronic control submeans which are each associated with the actuating means and sensors of each framework.

17. The device as claimed in claim 12, further comprising:

a second sensor means common to the plurality of frameworks.

18. The device as claimed claim 12, further comprising:

a plurality of means for fastening, each framework being fastened to the duct by a corresponding one of the means for fastening, each framework constituting a partitioning of the duct.

* * * * *